(12) United States Patent
Heaton

(10) Patent No.: US 9,408,751 B2
(45) Date of Patent: *Aug. 9, 2016

(54) MULTI-LUMEN CONNECTOR

(71) Applicant: KCI Licensing, Inc., San Antonio, TX (US)

(72) Inventor: Keith Patrick Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 192 days.

This patent is subject to a terminal disclaimer.

(21) Appl. No.: 14/248,812

(22) Filed: Apr. 9, 2014

(65) Prior Publication Data

US 2014/0236108 A1    Aug. 21, 2014

Related U.S. Application Data

(63) Continuation of application No. 13/661,803, filed on Oct. 26, 2012, now Pat. No. 8,740,878, which is a continuation of application No. 12/498,212, filed on Jul. 6, 2009, now Pat. No. 8,323,265, which is a continuation of application No. 10/129,900, filed as application No. PCT/GB00/04278 on Nov. 8, 2000, now Pat. No. 7,678,102.

(30) Foreign Application Priority Data

Nov. 9, 1999  (GB) .................................. 9926538.1

(51) Int. Cl.
*A61M 27/00*  (2006.01)
*A61F 13/00*  (2006.01)
(Continued)

(52) U.S. Cl.
CPC .......... *A61F 13/00068* (2013.01); *A61M 1/008* (2013.01); *A61M 1/0025* (2014.02);
(Continued)

(58) Field of Classification Search
CPC .......... A61F 13/00068; A61M 1/0031; A61M 1/008; A61M 1/0088; A61M 27/00
USPC .................. 604/317–328, 540, 543, 304–308
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Michele M Kidwell

(57) ABSTRACT

Apparatus is disclosed for applying negative pressure to a wound site to promote healing. The apparatus includes a porous pad for application to the wound, a suction tube linking the porous pad to a source of negative pressure, a container for collecting fluid exudate from the wound interposed between the porous pad and the source of negative pressure and a quick disconnect connector linking a first section of the suction tube leading to the porous pad with a second section leading to the container, said connector comprising two separable and non-interchangeable parts, said first section of the suction tube comprising a multi-lumen tube, one lumen being provided for applying suction to the porous pad and another being provided for monitoring pressure, said multi-lumen tube being fixedly attached at one end to the container and at the other end to one of said separable parts, said one separable part including sealing means whereby the lumens are connected in air-tight manner to said second section of the suction tube.

26 Claims, 6 Drawing Sheets

(51) Int. Cl.
*A61M 1/00* (2006.01)
*A61M 39/10* (2006.01)

(52) U.S. Cl.
CPC ............ *A61M1/0088* (2013.01); *A61M 27/00* (2013.01); *A61M 1/0031* (2013.01); *A61M 1/0037* (2013.01); *A61M 39/10* (2013.01); *A61M 39/105* (2013.01); *A61M 2205/3344* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov, Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

MULTI-LUMEN CONNECTOR

CROSS-REFERENCE TO RELATED APPLICATIONS

This application is a continuation of U.S. patent application Ser. No. 13/661,803, filed Oct. 26, 2012, which is a continuation of U.S. patent application Ser. No. 12/498,212, filed Jul. 6, 2009, now U.S. Pat. No. 8,323,265 which is a continuation of U.S. patent application Ser. No. 10/129,900, filed Mar. 15, 2004, now U.S. Pat. No. 7,678,102 which is a national stage application of International Application No. PCT/GB00/04278, filed Nov. 8, 2000, which claims the benefit of Great Britain Patent Application No. 9926538.1, filed Nov. 9, 1999. All of the above-referenced applications are hereby incorporated by reference.

BACKGROUND OF THE INVENTION

1. Field of the Invention

This invention relates to apparatus for applying negative pressure therapy to a wound. Negative pressure therapy is based on the observation that the application of continuous or intermittent suction to an open wound stimulates the rate of healing of the wound, probably by stimulating flow of blood in the zone of statis of the wound. It has now been accepted as a highly effective way of improving the rate of healing of patients suffering from pressure sores, ulcers, partial thickness burns and wounds that fail to heal quickly after an operation.

2. Description of Related Art

PCT Application WO 96/05873 describes apparatus for applying negative pressure therapy to a wound including a porous pad connected to a suction line with a collection container interposed between the suction means and the porous pad to collect exudate from the wound. UK Patent Application 9623743.3 (Publication No. 2307180) discloses a development of the apparatus described in the above PCT Application which provides for sensing pressure actually applied to the wound at the wound site. While the equipment described in the above application works effectively, disadvantages can occur in practice when there is a need to disconnect and reconnect the patient to the suction line.

SUMMARY

The present invention provides an improved apparatus which includes a convenient system for connecting and disconnecting the suction line to the wound site.

According to one aspect of the present invention there is provided apparatus or applying negative pressure therapy to a wound which comprises a porous pad for application to the wound, a suction tube linking the porous pad to a source of negative pressure, a container for collecting fluid exudate from the wound interposed between the porous pad and the source of negative pressure and a quick disconnect connector linking a first section of the suction tube leading to the porous pad with a second section leading to the container, said connector comprising two separable and non-interchangeable parts, said second section of the suction tube comprising a multi-lumen tube, one lumen being provided for applying suction to the porous pad and another being provided for monitoring pressure, said multi-lumen tube being fixedly attached at one end to the container and at the other end to one of said separable parts, said one separable part including sealing means whereby the lumens are connected in air-tight manner to said first section of the suction tube.

Preferably, also, the section of tube leading to the porous pad is a multi-lumen tube and is also fixedly attached to the separable connector part and to an adapter which can be sealed to the porous pad.

By the term "fixedly attached" we mean that the components mentioned are joined one to the other in such a way that they cannot be separated without damaging one or both of the joined components. The parts of the connector and the suction tube are generally formed from plastics material and the components can be fixedly joined by welding or adhesively. A convenient way of fixedly attaching the components is by using a mutual solvent for the components.

An advantage of the invention is that the container assembly and fixedly attached suction tube can only be used in conjunction with a correct, matching suction tube section and associated porous pad. Consequently, a proper and effective seal will be made between the two sections of the lumens for applying suction and the "sensor" lumen in one section will be sealing, connected to the corresponding sensor lumen in the other section or to the "suction" lumen in that section. As a result, the pressure at or close to the wound site can be reliably monitored.

BRIEF DESCRIPTION OF THE DRAWINGS

Various other aspects, features and advantages of the present invention will become apparent from the following description and accompanying drawings, in which.

DETAILED DESCRIPTION OF ILLUSTRATIVE EMBODIMENTS

Figure 1:
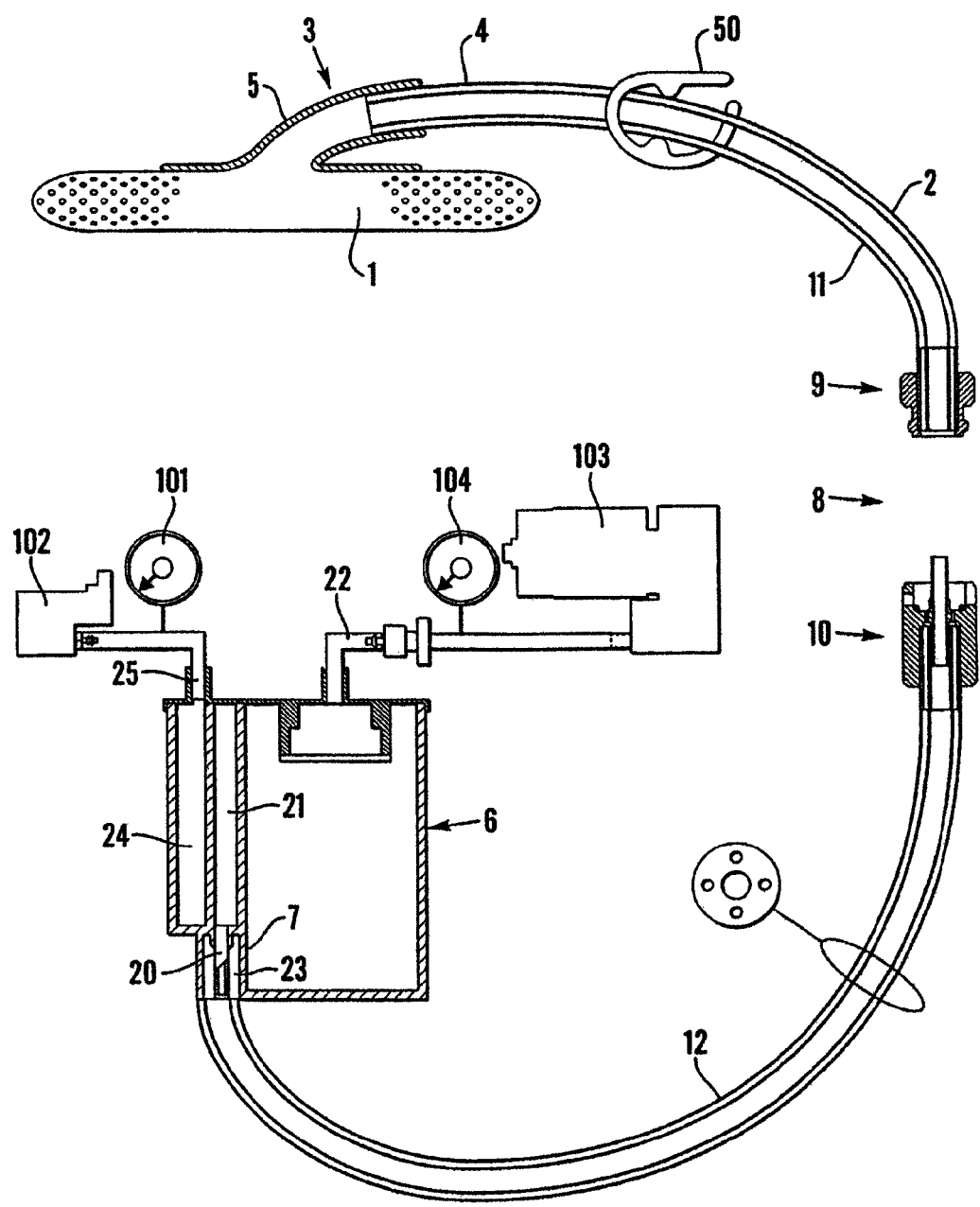
FIG. 1 is a part schematic view of apparatus in accordance with the invention.

Referring to the drawings and, in particular, FIG. 1, the apparatus in accordance with the invention comprises a porous pad (1) (e.g. of polymeric, open-celled foam, such as a polyurethane or polyvinyl alcohol foam having interconnected cells), intended for application into or onto a wound to be treated. The porous pad is connected to a source of negative pressure (103) such as a pump or vacuum bottle by a suction tube (2) and adapter (3) in the manner described generally in our above British Application No. 2307180 and our pending UK Patent Application No. 9819673.5 (Publication No. 2329127. The adapter (3) is preferably constructed in the manner shown in UK Patent Application No. 9819678.5 (Publication No. 2329127 and the porous pad and the adapter (3) are sealed in airtight manner to the wound site, using a surgical drape as described in UK Patent Application No. 2307130 or No. 2329127. Suction tube (2) is fixedly attached at one end (4) to a spout portion (5) of the adapter (3). The end (4) may be sealed and fixed by any suitable means such as welding or adhesive bonding to the spout (5). Conveniently, an adhesive bond may be formed by applying a solvent for the material of the adapter and the suction tube to the outer surface of the tube and inserting the tube into the adapter. The other end of suction tube (2) is connected to a wound exudate container (6) where it is fixedly sealed in airtight manner to the inlet end (7) of the container by suitable means. Suction tube (2) is formed in two parts which are linked by a connector (8). Connector (8) comprises two easily separable parts (9) and (10) which enables the patient to be easily and quickly disconnected from the major part of the apparatus, e.g. for ease of moving the patient for other treatment. The section (11) of the suction tube (1) which links the adapter (3) to the connector half (9) extends fully into the connector half (9) and is sealed therein, e.g. by adhesive bonding or welding. Thus, the section of tube (11) is sealed at both of its ends.

Similarly, the second section of suction tube (12) which links the connector half (10) with the collection container (6) is also sealed into its respective connector half (10). Thus, no air leaks are possible between the adapter and the connector (8) and between the connector (8) and the container (6). Connector (8) is designed so that the two halves when assembled are locked together in a sealed condition. The construction of the connector will be described in more detail below.

The section (12) of suction tube (2) is a multi-lumen tube having a central lumen for applying suction to the wound site and one or more peripheral lumens for sensing pressure at the wound site. Specific examples of multi-lumen tubes are described in our co-pending British Patent Application No. 9819678.5 (Publication No. 2329127).

Preferably, also, the section (11) is a multi-lumen tube, but this is not essential especially if the section (11) between the connector half (9) and the patient is a relatively short piece. In that case, the pressure sensed at the connector (8) will be essentially the same as the pressure sensed at the wound site.

At the container (6) the central lumen is connected to a tube (20) which is linked by passage (21) to the interior of the container (6). Suction may, be applied to the container, e.g. through a tube (22) to apply suction to the wound site. The outer lumen or lumens communicate with a peripheral passage (23) which is connected to a chamber (24). Chamber (24) is linked by a port (25) to a transducer (10) for measuring pressure at the connector (8) or at the wound site (1). A valve (102) may also be connected to the port (25) and can be opened to atmosphere to release or reduce the negative pressure at the wound site. By opening or closing the valve (102) at intervals, intermittent or varying negative pressure can be applied at the wound.

Tube (22) is connected to a source of negative pressure, e.g. pump (103). A pressure sensor (104) is connected to the tube (22) to sense the pressure in the suction line.

The connector is shown in more detail in FIGS. 2 to 5 of the accompanying drawings.

Figure 2:
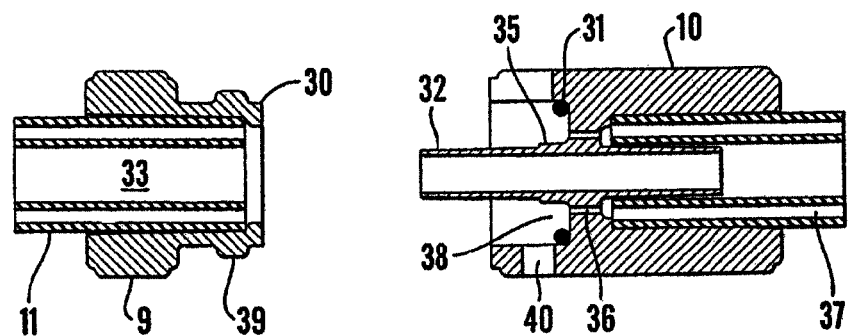
FIG. 2 shows the two separable parts of the connector with portions of multi-lumen tubes fitted to them.
Figure 3:
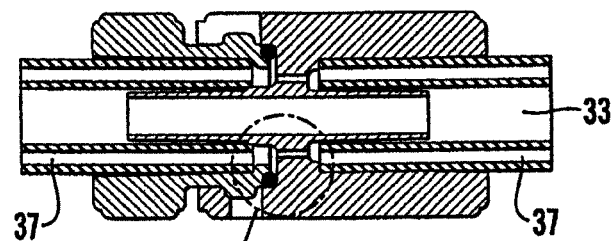
FIG. 3 shows the two halves of the connector fitted together.
Figure 3A:
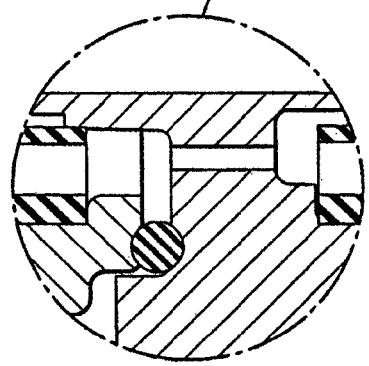
FIG. 3a is an enlarged portion of the part indicated in FIG. 3.
Figure 4:
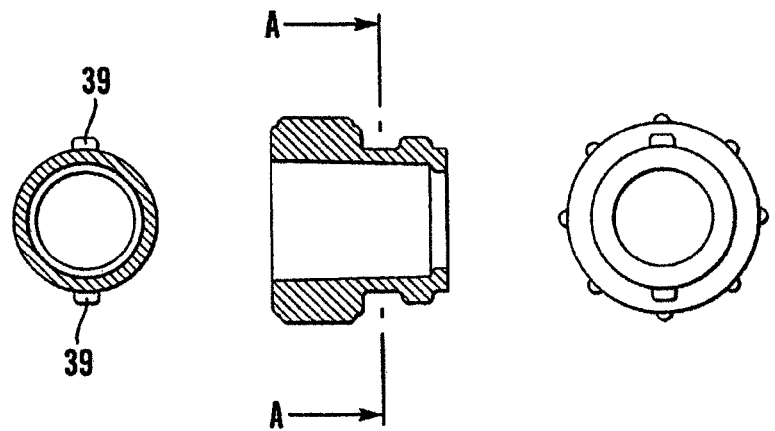
FIGS. 4 and 5 show views of the two connector halves from various viewpoints.
Figure 5:
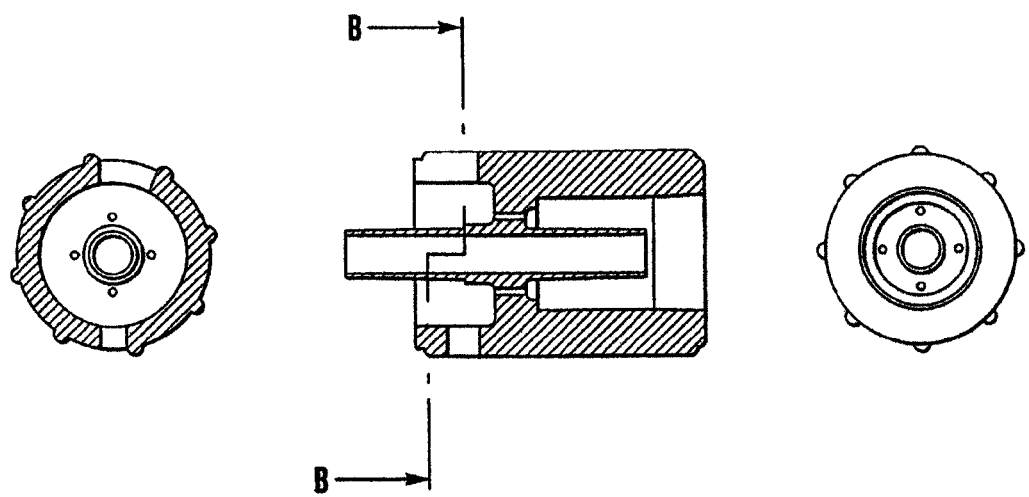

Referring to FIG. 2 it will be seen that the connector half (9) has a shoulder (30) which enters a recess within the connector half (10) and seals against an O-ring Connector half (10) has a projecting tubular part (32) which is dimensioned to enter the central lumen (33) of the multi-lumen tube (11), and in the fully assembled condition of the connector, the enlarged portion (35) seals within the central lumen (33). Connector half (10) has passages (36) which communicate at one end with one or more peripheral lumens (37), and at the other with a space (38) outside the central projection (32).

The two halves (9) and (10) are held together in their closed position by a bayonet-type fitting comprising a projection (39) which engages in a slot (40). The inter-engaging surfaces forming the slot and the projection (39) are such that the two halves are forced together so as to compress the O-ring (31) and force the portion (35) firmly into the inner lumen (33). The position is shown clearly in FIG. 3 in the assembled condition. It will be seen that when assembled, the central lumen (33) communicates through the hollow projecting portion (32) between the two portions of the multi-lumen tube and this path is quite separate from the sensor part which connects the lumens (37) in each section of the suction tube.

Suitable materials for manufacturing the tubing include pvc, and suitable materials for manufacturing the connector include pvc, polypropylene and ABS. The tubes may be sealed into the connector halves by means of a solvent glue such as a cyclohexanol glue, or by a UV light curable adhesive composition. In order to prevent the sections (11) and (12) of the multi-lumen tube from leaking when disassembled, clamps (50) may be applied to the tube prior to separating the two halves of the connector.

Figure 6:
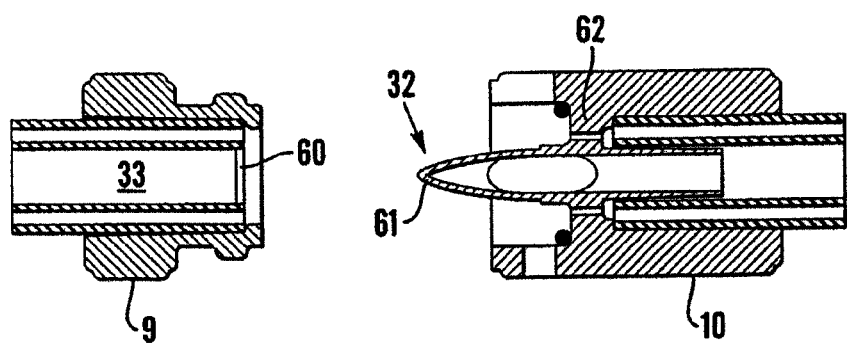
FIG. 6 shows a modification of the connector.

FIG. 6 shows a modification of the connector which provides an automatic sealing effect when the two halves are disconnected. This connector is essentially the same as the connector shown in FIGS. 2 and 3, and differs by having a rubbery membrane (16) across the central part (33) of the multi-lumen tube or across the whole of the open end of the suction tube portion (11). The projecting part (32) of the connector half (10) is shaped with a needle end (61), which is capable of piercing the rubber membrane (60). The projecting portion (32) has a lateral orifice (62) communicating with its hollow interior. Thus, when the two parts (9) and (10) are brought together, the needle end (61) penetrates the membrane (60) and places the two central lumens of the suction tubes (11) and (12) into communication. The membrane (60) is designed to be a soft material which self-seals when the portion (32) is withdrawn, thus preventing exudate from leaking from the end of the tube (11) when it is disconnected from the connector half (10).

In some circumstances where, for example, a very large wound is being treated, or simultaneous treatment is required perhaps to two sides of one limb, either separate porous pads will be appropriate, or a very large porous pad will be necessary. In such circumstances, it may be convenient to provide two adapters (5) which are both connected by tubing (11) to a suction device and drainage container (6). In these circumstances, rather than connect the tubing separately to the container, a Y- or T-shaped connector piece may be provided in which two arms are connected to separate tubes (11), leading to separate adapters and the third arm (10) is connected to the collection container. Two Y-shaped connectors are shown in FIG. 7. The arms of the Y-shaped connector body piece (100) are each provided with a separable part (80 or 81) which will each connect to a corresponding part fixedly attached to a respective tubing section.

Figure 7A:
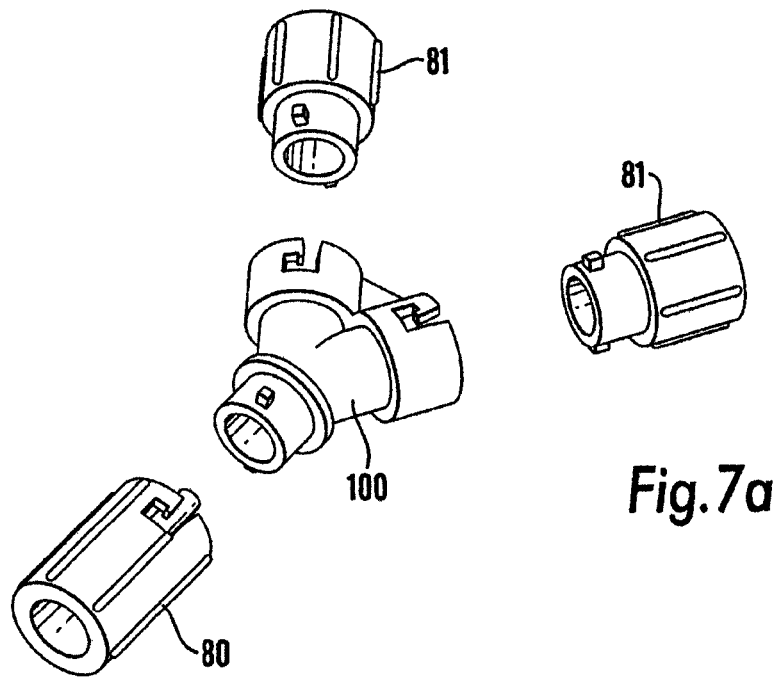
FIGS. 7a and 7b shows perspective views of a 3-way connector.
Figure 7B:
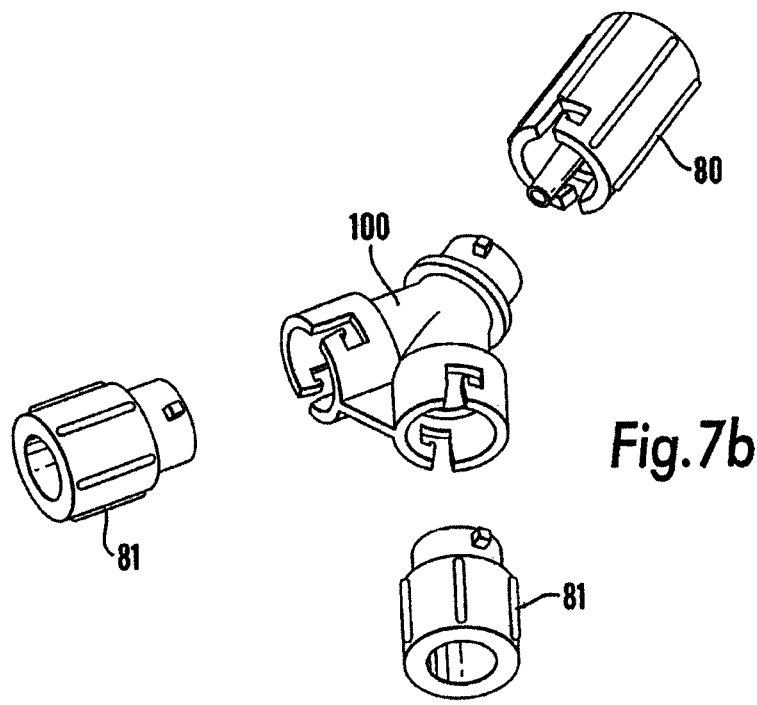

Connector part (80) is attached to a multi-lumen tube section and the other end of the multi-lumen section is sealed to a canister (6). The other connector parts may be fixedly attached to other sections of the suction tube each of which lead to an adapter (3). For a large wound, two adapters may be arranged to apply suction to the same wound. While the sections of suction tube leading from the 'Y' piece to the adapters may be multi-lumen tubes, this is not essential and would require a very complex moulding for the 'Y' piece. Although, in this case, the pressure sensed at the wound site will be the average of the pressures at the two adapters, they will normally be close enough together for the pressure difference to be small FIGS. 7A and 7B show the bayonet fitting very clearly.

Figure 8A:
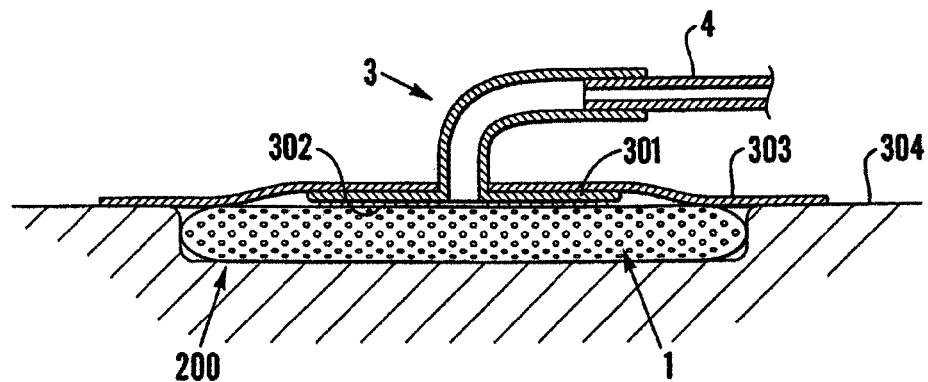
FIGS. 8a, 8b and 8c show modified forms of the adaptor and systems for sealing the adaptor to a wound site.
Figure 8B:
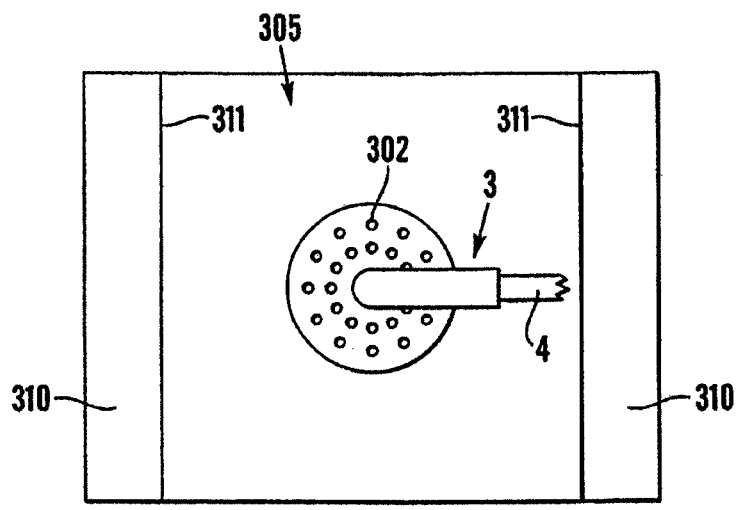
Figure 8C:
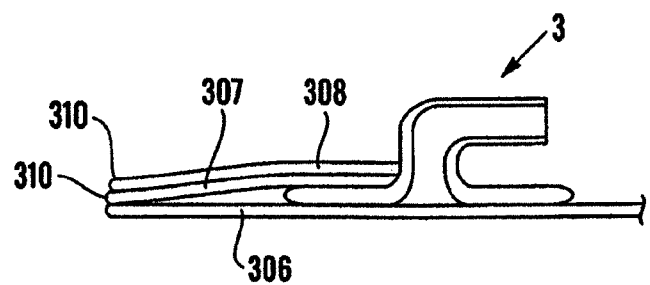

FIGS. 8A, 8B and 8C show the arrangement of sealing the adapter assembly to a wound. FIG. 8A is a section through the adapter assembly attached to a wound (200). A porous dressing (1) e.g. of polyurethane foam is packed into the wound cavity and an adapter (3) is pressed against the surface of the dressing. As can be seen from FIGS. 8A-8C, the underside of the flange 301 of the adaptor is covered with projections (302), which are arranged in a staggered disposition to facilitate flow of fluids from a wide area of the foam pad (1) into the spout (5) of the adapter. The adapter (3) and dressing are sealed into the wound cavity by a thin elastomeric sheet material (303) which is adhered by a tacky pressure-sensitive adhesive to the skin (304) surrounding the wound (200). Sheet material (303) is typically polyurethane film which is coated all over one face with adhesive so that it is bonded to the upper face of flange (301) as well as to the skin of the patient.

FIG. 8B is a plan view from above of the adapter showing the surgical drape assembly (305) surrounding the adapter. The drape assembly and the flange of the adapter are transparent so that the projections (302) can be seen. The drape assembly comprises three layers of sheet material as best seen in FIG. 8C. The lower-most layer (306) is a release-coated comparatively stiff sheet material which is lightly bonded to, the lower, adhesive-coated face of the surgical drape itself (307). The latter material is a very thin, flexible elastomeric material. A strengthening layer (308) of thicker material overlies the drape layer (307). Layers (307) and (308) have holes to permit the spout (5) of the adapter to pass through. In use, the foam pad (1) is placed in the wound, the release layer (306) is removed and the adhesive face of the drape applied to the skin around the pad to produce an airtight seal. Strengthening layer (308) is removed prior to, during or after adhering the drape to the skin. Handling bars (310) of thicker material are attached to the ends of the drape layer and to the ends of the strengthening layer to facilitate adhering the drape to the skin and separating the strengthening layer from the drape. After the seal has been achieved, the handling bars can be removed from the drape layer and perforations (311) may be provided for this purpose.

I claim:

1. Apparatus for providing negative pressure to a wound through an adapter, comprising:
    a first tube comprising a single lumen tube having first end adapted to be fluidly connected to the adapter for providing reduced pressure and a second end,
    a second tube comprising at least two lumens, a first lumen having a first end adapted to be fluidly connected to a pressure sensor and a second end, and a second lumen having a first end adapted to be fluidly connected to a source of reduced pressure and a second end; and
    a connector comprising a first part and a second part, each part having a first end fluidly linkable and sealable to the other, the first part having a second end fluidly connected to the second end of the first tube, and the second part having a second end fluidly connected to the second ends of the first lumen and the second lumen of the second tube.

2. The apparatus of claim 1, wherein the adapter includes a flange portion adapted to apply reduced pressure to the wound, and a spout portion adapted to be fluidly coupled between the flange portion and the first end of the first tube.

3. The apparatus of claim 1, wherein the first part and the second part of the connector include linkable parts of a bayonet fitting for connection and disconnection.

4. The apparatus of claim 1, wherein the first end of the first part is sealably connectable to the first end of the second part by a tubular projection attached to the second part, the tubular projection adapted to extend through the first part into the single lumen and form a sealed engagement with the single lumen.

5. The apparatus of claim 4, wherein the tubular projection has a needle end.

6. The apparatus of claim 1, wherein the second tube has a side-by-side lumen configuration.

7. The apparatus of claim 1, wherein the second tube has a coaxial lumen configuration.

8. The apparatus of claim 1, further comprising a container positioned between the source of reduced pressure and the adapter, wherein the first part and the second part couple to form a seal between the adapter and the container.

9. The apparatus of claim 1, wherein the second lumen of the second tube connected to the source of reduced pressure is a central lumen.

10. The apparatus of claim 9, further comprising a sensor to measure pressure within the central lumen.

11. The apparatus of claim 1, wherein the first lumen of the second tube fluidly connected to the pressure sensor is a peripheral lumen.

12. The apparatus of claim 11, wherein the pressure sensor measures pressure through the peripheral lumen at least at one of the following locations: the wound, adjacent the wound, and proximal the wound.

13. The apparatus of claim 1, wherein at least a portion of the first part and the second part is made from at least one of PVC, polypropylene, and ABS.

14. Apparatus for providing negative pressure to a wound through an adapter, comprising:
    a first tube comprising at least two lumens, a first lumen having a first end adapted to be in fluid communication with the adapter to sense pressure and a second end, and a second lumen having a first end adapted to be fluidly connected to the adapter for providing reduced pressure and a second end,
    a second tube comprising at least two lumens, a first lumen having a first end adapted to be fluidly connected to a pressure sensor and a second end, and a second lumen having a first end adapted to be fluidly connected to a source of reduced pressure and a second end; and
    a connector comprising a first part and a second part, each part having a first end fluidly linkable and sealable to the other, the first part having a second end fluidly connected to the second ends of the first and second lumens of the first tube, and the second part having a second end fluidly connected to the second ends of the first and the second lumens of the second tube.

15. The apparatus of claim 14, wherein the adapter includes a flange portion adapted to apply reduced pressure to the wound, and a spout portion adapted to be fluidly coupled between the flange portion and the first end of the second lumen of the first tube.

16. The apparatus of claim 14, wherein the first part and the second part of the connector include linkable parts of a bayonet fitting for connection and disconnection.

17. The apparatus of claim 14, wherein the first end of the first part is sealably connectable to the first end of the second part by a tubular projection attached to the second part, the tubular projection adapted to extend through the first part into the second lumen and form a sealed engagement with the second lumen.

18. The apparatus of claim 17, wherein the tubular projection has a needle end.

19. The apparatus of claim 14, wherein the first tube and the second tube have a side-by-side lumen configuration.

20. The apparatus of claim 14, wherein the first two and the second tube have a coaxial lumen configuration.

21. The apparatus of claim 14, further comprising a container positioned between the source of reduced pressure and the adapter, wherein the first part and the second part couple to form a seal between the adapter and the container.

22. The apparatus of claim 14, wherein the second lumen of the second tube connected to the source of reduced pressure is a central lumen.

23. The apparatus of claim 22, further comprising a sensor to measure pressure within the central lumen.

24. The apparatus of claim 14, wherein the first lumen of the second tube fluidly connected to the pressure sensor is a peripheral lumen.

25. The apparatus of claim 24, wherein the pressure sensor measures pressure through the peripheral lumen at least at one of the following locations: the wound, adjacent the wound, and proximal the wound.

26. The apparatus of claim 1, further comprising an O-ring wherein the first end of the first part is sealably connectable to the first end of the second part by the O-ring.

\* \* \* \* \*